US009226671B2

(12) United States Patent
Cho et al.

(10) Patent No.: US 9,226,671 B2
(45) Date of Patent: Jan. 5, 2016

(54) APPARATUS AND METHOD FOR MEASURING BLOOD FLOW

(75) Inventors: Young-Ho Cho, Daejeon (KR);
Jai-Kyoung Sim, Daejeon (KR);
Se-Chan Youn, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 13/432,449

(22) Filed: Mar. 28, 2012

(65) Prior Publication Data

US 2012/0253205 A1 Oct. 4, 2012

(30) Foreign Application Priority Data

Mar. 30, 2011 (KR) ........................ 10-2011-0028749

(51) Int. Cl.
*A61B 5/026* (2006.01)
*A61B 5/00* (2006.01)
*A61B 5/117* (2006.01)
*A61B 5/1491* (2006.01)

(52) U.S. Cl.
CPC .............. *A61B 5/026* (2013.01); *A61B 5/0261* (2013.01); *A61B 5/1172* (2013.01); *A61B 5/6843* (2013.01); *A61B 5/1491* (2013.01)

(58) Field of Classification Search
CPC .. A61B 5/6843; A61B 5/1172; A61B 5/0261; A61B 5/1491; A61B 5/026; A61B 5/01

USPC ................................................... 600/454, 504
See application file for complete search history.

(56) References Cited

U.S. PATENT DOCUMENTS

| 4,859,078 A * | 8/1989 | Bowman et al. ................. 374/44 |
| 6,554,774 B1 * | 4/2003 | Miele ............................ 600/504 |
| 7,682,317 B2 * | 3/2010 | Bowman et al. .............. 600/549 |
| 2010/0225926 A1 * | 9/2010 | van Amstel et al. .......... 356/511 |

OTHER PUBLICATIONS

Bambi et al., "A novel ultrasound instrument for investigation of arterial mechanics". Ultrasonics. 42. 2004. pp. 731-737.*
Burcher et al., "A System for Simultaneously Measuring Contact Force, Ultrasound, and Position Information for Use in Force-Base Correction of Freehand Scanning". IEEE Transactions on Ultrasonics, Ferroelectrics, and Frequency Control. vol. 52, No. 8. Aug. 2005. pp. 1330-1342.*

(Continued)

*Primary Examiner* — Long V Le
*Assistant Examiner* — Colin T Sakamoto
(74) *Attorney, Agent, or Firm* — Harness, Dickey & Pierce, P.L.C.

(57) ABSTRACT

An apparatus for measuring blood flow includes a detection part and a signal processing part. The detection part includes a blood flow detector for measuring a blood flow of a measured portion of an object, which makes contact with the measured portion, and a force detector for detecting a contact force between the blood flow detector and the measured portion. The signal processing part produces a corrected blood flow in reflection of an error of the blood flow due to the contact force.

18 Claims, 3 Drawing Sheets

(56) References Cited

OTHER PUBLICATIONS

Maxim Integrated. "Tutorial 928, Filter Basics: Anti-Aliasing". Jan. 11, 2002. retrieved Aug. 9, 2013 from <http://www.maximintegrated.com/app-notes/index.mvp/id/928>.*

Cyanogen. "Low-Pass Filtering". archived by WayBack Machine Jul. 2, 2004. retrieved Aug. 9, 2013. <http://web.archive.org/web/20040702075951/http://cyanogen.com/help/maximdl/Low-Pass_Filtering.htm>.*

* cited by examiner

APPARATUS AND METHOD FOR MEASURING BLOOD FLOW

CLAIM OF PRIORITY

This application claims priority under 35 USC §119 to Korean Patent Application No. 2011-0028749, filed on Mar. 30, 2011 in the Korean Intellectual Property Office (KIPO), the contents of which are herein incorporated by reference in their entirety.

BACKGROUND

1. Field

Example embodiments relate to an apparatus and a method for measuring blood flow. More particularly, example embodiments relate to an apparatus and a method for measuring blood flow by contacting skin.

2. Description of the Related Art

The blood flow of the skin is related to a thermal equilibrium of a body. When the body feels the heat, the blood flow of the skin may increase so that the heat may be emitted. When the body feels the cold, the blood flow of the skin may decrease so that the radiation of the heat may be prevented. Thus, the thermal equilibrium of the body may be detected by monitoring the blood flow of the skin. The skin blood flow of terminal portions of the body, e.g., fingers, toes, earlobes, etc. may be reacted by the heat and/or the cold more sensitively than other portions of the body. Accordingly, developing a blood flow sensor for measuring a skin blood flow at the terminal portions of the body may lead to developing a system for detecting the thermal equilibrium of the body.

The conventional blood flow sensors are mainly used on a clinical experiment in a hospital and have a large size. Additionally, the blood flow sensors are used after they are fastened to a specific portion of the body by attaching or winding because the blood flow may change according to the contact force between the blood flow sensors and the measured portion. However, fastening the blood flow sensors to the specific portion of the body may cause inconvenience to the user.

Thus, an apparatus and a method for measuring blood flow without errors due to the contact are needed even without fastening the blood sensor to the body.

SUMMARY

Example embodiments provide an apparatus for measuring blood flow, wherein the apparatus may measure the blood flow exactly even without fastening a blood flow sensor to a body.

Example embodiments provide a method for measuring blood flow in which the blood flow may be exactly measured even without fastening a blood flow sensor to a body.

According to example embodiments, there is provided an apparatus for measuring blood flow. The apparatus includes a detection part and a signal processing part. The detection part includes a blood flow detector for measuring a blood flow of a measured portion of an object, which makes contact with the measured portion, and a force detector for detecting a contact force between the blood flow detector and the measured portion. The signal processing part produces a corrected blood flow in reflection of an error of the blood flow due to the contact force.

In example embodiments, the blood flow detector may include a heater for heating the measured portion and a thermometer for measuring a temperature of the measured portion.

In example embodiments, the blood flow detector may include a light source for emitting a light onto the measured portion and a light sensor for detecting a light reflected from the measured portion.

In example embodiments, the force detector may include a piezoelectric element or a capacitive sensor.

In example embodiments, the signal processing part may include a contact force-blood flow change model producer for producing a contact force-blood flow change model by modeling a blood flow change due to a contact force, an error calculator for calculating the error of the blood flow due to the contact force using the contact force-blood flow change model, a correction calculator for producing the corrected blood flow in reflection of the calculated blood flow error, a blood flow calculator for calculating a blood flow from a signal transferred by the blood flow detector, and a contact force calculator for calculating a contact force from a signal transferred by the force detector.

In example embodiments, the apparatus may further include a storage part for storing data generated by the detection part and the signal processing part.

In example embodiments, the apparatus may further include a display part for displaying data generated by the signal processing part.

In example embodiments, the apparatus may further include a user identification part for identifying a user having the measured portion.

According to example embodiments, there is provided a method of measuring blood flow. In the method, i) a blood flow is measured by contacting a blood flow detector with a measured portion of an object, and a contact force between the blood flow detector and the measured portion is measured. ii) An error of the blood flow due to the contact force is calculated using the measured contact force. iii) A corrected blood flow is produced in reflection of the calculated blood flow error.

In example embodiments, when the blood flow and the contact force are measured, an average blood flow and an average contact force, respectively, may be measured during a given time.

In example embodiments, when the blood flow and the contact force are measured, the contact force may be filtered so that the contact force not within a given range may be excluded.

In example embodiments, when the blood flow error is calculated, the calculation may be performed using a blood flow change model due to a contact force.

In example embodiments, when the corrected blood flow is produced, the measured blood flow may be corrected to a blood flow at a reference contact force by reflecting the calculated blood flow error to the blood flow measured at the contact force.

In example embodiments, if the measured contact force is within a given range, the steps of i) to iii) may be repeatedly performed.

In example embodiments, a user having the measured portion may be identified.

In example embodiments, whether or not a contact force-blood flow change model of the user exists may be confirmed.

In example embodiments, if a contact force-blood flow change model of the user is not confirmed, a contact force-blood flow change model may be produced by measuring a blood flow of the measured portion while changing a contact force between the blood flow detector and the measured portion, and the contact force-blood flow change model may be stored.

According to example embodiments, the apparatus for measuring blood flow may include a blood flow detector and a force detector, and thus may measure a contact force while measuring a blood flow. A signal processing part of the apparatus may calculate an error of the blood flow due to the contact force, and reflect the blood flow error to the measured blood flow. Thus, more exact blood flow may be produced.

BRIEF DESCRIPTION OF THE DRAWINGS

Example embodiments will be more clearly understood from the following detailed description taken in conjunction with the accompanying drawings. FIGS. 1 to 16 represent non-limiting, example embodiments as described herein.

FIG. 1 is a block diagram illustrating an apparatus for measuring blood flow in accordance with example embodiments;

FIGS. 2 and 3 are cross-sectional views illustrating first and second detection parts, respectively, included in the apparatus for measuring blood flow of FIG. 1; and FIG. 4 is a flowchart illustrating a method of measuring blood flow using the blood flow measurement apparatus of FIG. 1 in accordance with example embodiments.

DESCRIPTION OF EMBODIMENTS

Figure 1:
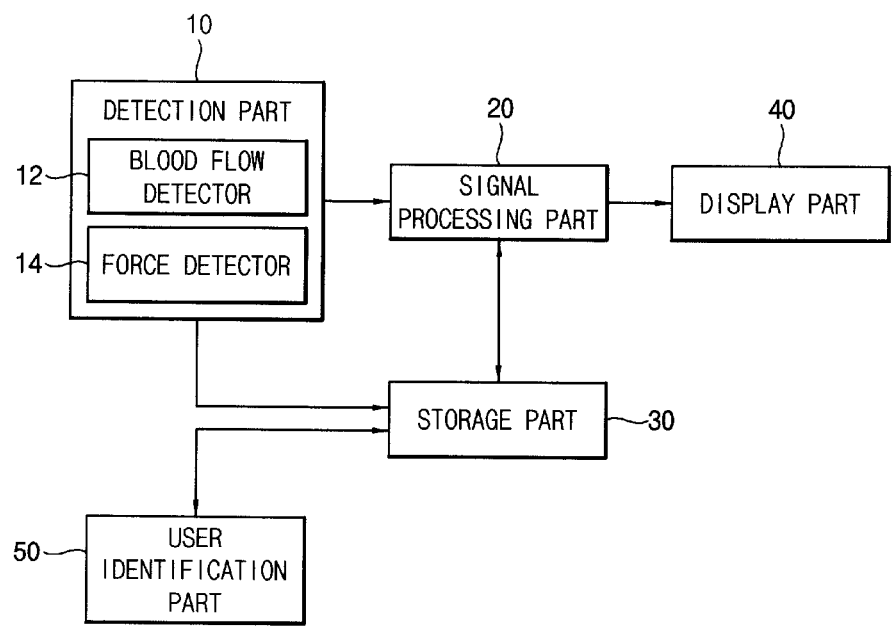

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this description will be thorough and complete, and will fully convey the scope of the present inventive concept to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, fourth etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concept.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a block diagram illustrating an apparatus for measuring blood flow in accordance with example embodiments.

Referring to FIG. 1, the apparatus for measuring blood flow may include a detection part 10 and a signal processing part 20. The apparatus may further include a storage part 30, a display part 40 and a user identification part 50.

The detection part 10 may include a blood flow detector 12 and a force detector 14.

The blood flow detector 12 may contact a portion of an object, e.g., a portion of a human body of which a blood flow may be measured.

The force detector 14 may detect a contact force between the blood flow detector 12 and the measured portion of the object.

In example embodiments, the blood flow data and the contact force data detected by the blood flow detector 12 and the force detector 14, respectively, may be generated as an electrical signal.

Figure 2:
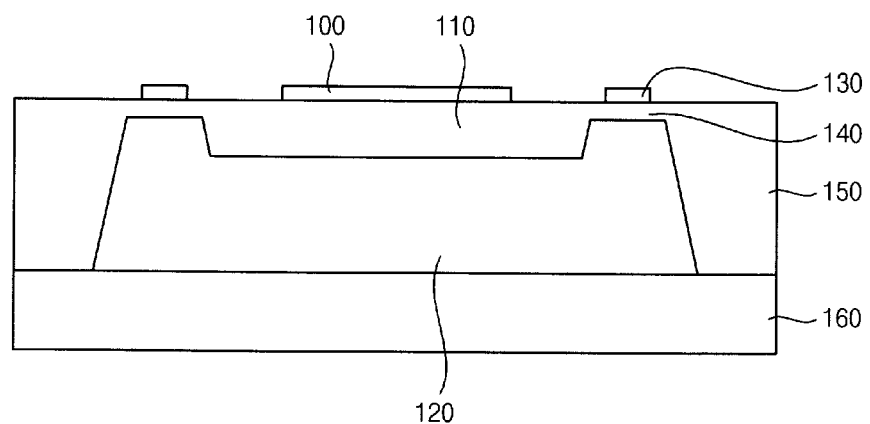
Figure 3:
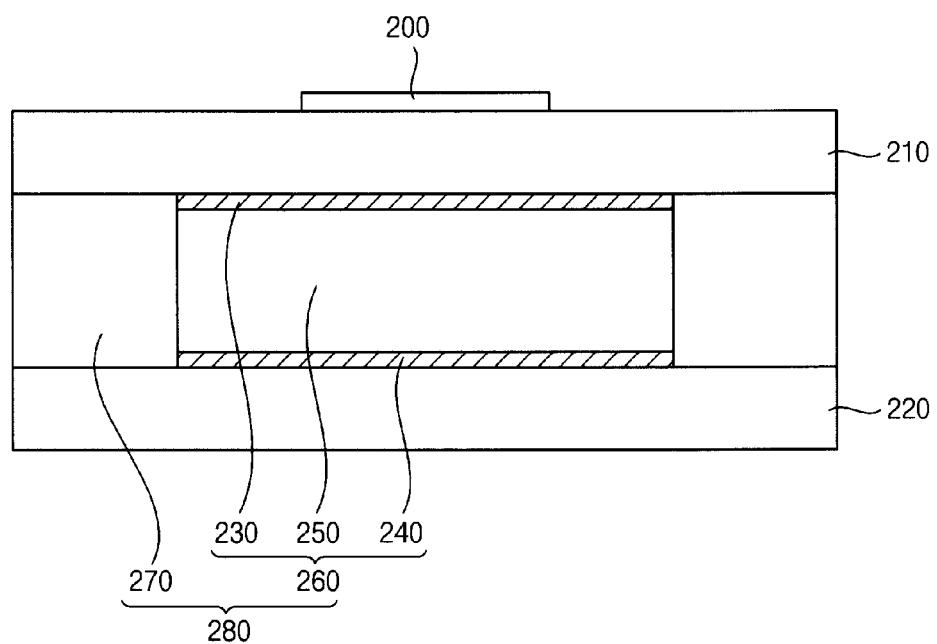

FIGS. 2 and 3 are cross-sectional views illustrating first and second detection parts, respectively, included in the apparatus for measuring blood flow of FIG. 1.

Referring to FIG. 2, the first detection part may include a first blood flow detector 100, which may detect blood flow by a thermal method, and a first force detector 130, which may detect force by a piezoelectric method.

The first blood flow detector 100 may include a heater (not shown) for applying heat to the measured portion of the object, and a thermometer (not shown) for detecting a temperature of the measured portion of the object. In an example embodiment, the first blood flow detector 100 may be mounted on an upper plate 110 making contact with the measured portion and be protruded therefrom. Alternatively, the first blood flow detector 100 may be placed in a recess (not shown) on the upper plate 110, and a top surface of the first blood flow detector 100 may be coplanar with a top surface of the upper plate 110.

When the heater heats the measured portion, the temperature of the measured portion may increase, however, the temperature of the measured portion may decrease again according to the blood flow of the measure portion. Thus, the blood flow may be measured by measuring a temperature change of the measured portion according to the lapse of time.

In order to guarantee the exactness of the blood flow detection by the thermal method, the loss of heat generated from the heater may be needed to be reduced. Thus, the upper plate 110 on which the first blood flow detector 100 is mounted may include a material of a low thermal conductivity and be surrounded by an adiabatic layer 120. In an example embodiment, the adiabatic layer 120 may include air.

The first force detector 130 may include a piezoelectric element. In example embodiments, the piezoelectric element may be mounted on a thin film 140 that may have a stress due to an external force. The thin film 140 may be formed adjacent to the upper plate 110 on which the first blood flow detector 100 is mounted, and be supported by a supporting member 150.

When the first blood flow detector 100 contacts the measured portion, the thin film 140 adjacent to the first blood flow detector 100 may also contact the measured portion, and the thin film 140 may have a stress due to a contact force between the measured portion and the thin film 140 so that a resistance of the piezoelectric element may change. Thus, the contact force may be measured by measuring the resistance change of the piezoelectric element.

The resistance of the piezoelectric element may change not only due to the stress but also due to temperature. Thus, the piezoelectric element may have a Wheatstone bridge circuit so that the resistance change due to the temperature may be corrected.

The adiabatic layer 120 and the supporting member 150 may be formed on a lower plate 160. The lower plate 160 may include a material of a low thermal conductivity.

Referring to FIG. 3, the second detection part may include a second blood flow detector 200, which may detect blood flow by an optical method, and a second force detector 280, which may detect force by a capacitive method.

The second blood flow detector 200 may include a light source (not shown) for emitting a light onto the measured portion, and a light sensor (not shown), which may detect a light reflected from the measured portion. In an example embodiment, the second blood flow detector 200 may be mounted on the upper plate 210 making contact with the measured portion and be protruded therefrom. Alternatively, the second blood flow detector 200 may be placed in a recess (not shown) on the upper plate 210, and a top surface of the second blood flow detector 200 may be coplanar with a top surface of the upper plate 210.

When a light generated from the light source is emitted onto the measured portion, an intensity of a light reflected from the measured portion may change according to a blood flow in the measured portion. Thus, the blood flow may be measured by measuring the intensity change of the light reflected from the measured portion.

The second force detector 280 may include a capacitance sensor.

The capacitance sensor may include a capacitor 260 and an elastic body 270.

The capacitor 260 may have an upper electrode 230, a lower electrode 240 and a dielectric substance 250 between the upper and lower electrodes 230 and 240. In example embodiments, the dielectric substance 250 may include air.

The elastic body 270 may be formed adjacent to the capacitor 260, and a relative position of the upper and lower electrodes 230 and 240 with respect to each other may change because of the elastic body 270.

In example embodiments, the capacitance sensor may be disposed between upper and lower plates 210 and 220. That is, the upper electrode 230 of the capacitor 260 may be disposed beneath a bottom surface of the upper plate 210, the lower electrode 240 of the capacitor 260 may be disposed on a top surface of the lower plate 220, and the elastic body 270 may be disposed between the upper and lower electrodes 210 and 220. Thus, the elastic body 270 may contract due to a contact force generated when the second blood flow detector 200 on the upper plate 210 contacts the measured portion, and a distance between the upper and lower electrodes 230 and 240 may be shorter. As a result, a capacitance of the capacitor 260 may increase. Thus, the contact force may be measured by measuring the capacitance.

So far, the detection part 10 including the first blood flow detector 100 operated by a thermal method and a first force detector 130 operated by a piezoelectric method, or the detection part 10 including a second blood flow detector 200 operated by an optical method and a second force detector 280 operated by a capacitive method has been illustrated, however, other combinations of the blood flow detector and the force detector may be possible. For example, the detection part 10 may include the first blood flow detector 100 and the second force detector 280 or may include the second blood flow detector 200 and the first force detector 130.

Referring to FIG. 1 again, the signal processing part 20 may include a blood flow calculator, a contact force calculator, a contact force-blood flow change model producer, an error calculator and a correction calculator, and may produce a corrected blood flow in reflection of the blood flow error due to the contact force. In example embodiments, the signal processing part 20 may include a computer or a microprocessor.

Particularly, the blood flow calculator and the contact force calculator of the signal processing part 20 may calculate a blood flow and a contact force from blood flow data and contact force data transferred by the blood flow detector 12 and the force detector 12, respectively. The blood flow calculator and the contact force calculator may calculate an instant blood flow and an instant contact force, respectively, or calculate an average blood flow and an average contact force, respectively, during a given time.

The contact force-blood flow change model producer may produce a contact force-blood flow change model using the calculated blood flow and contact force.

The error calculator may calculate an error of a blood flow due to the contact force using the produced contact force-blood flow change model.

The correction calculator may produce a corrected blood flow in reflection of the calculated blood flow error.

The storage part 30 may store data, signals, models, etc., produced by the detection part 10 and the signal processing part 20. The storage part 30 may store blood flow data and contact force data detected by the detection part 10, and may store a blood flow, a contact force, a contact force-blood flow change model, a blood flow error and a corrected blood flow calculated or produced by the signal processing part 20. The storage part 30 may further store fingerprints of users.

The display part 40 may display various signals produced by the signal processing part 20.

The user identification part 50 may identify a user having the measured portion. In example embodiments, the user identification part 50 may include a fingerprint recognizer (not shown), and may identify users by recognizing fingerprints of users and comparing the recognized fingerprints with fingerprints stored in the storage part 30.

Figure 4:
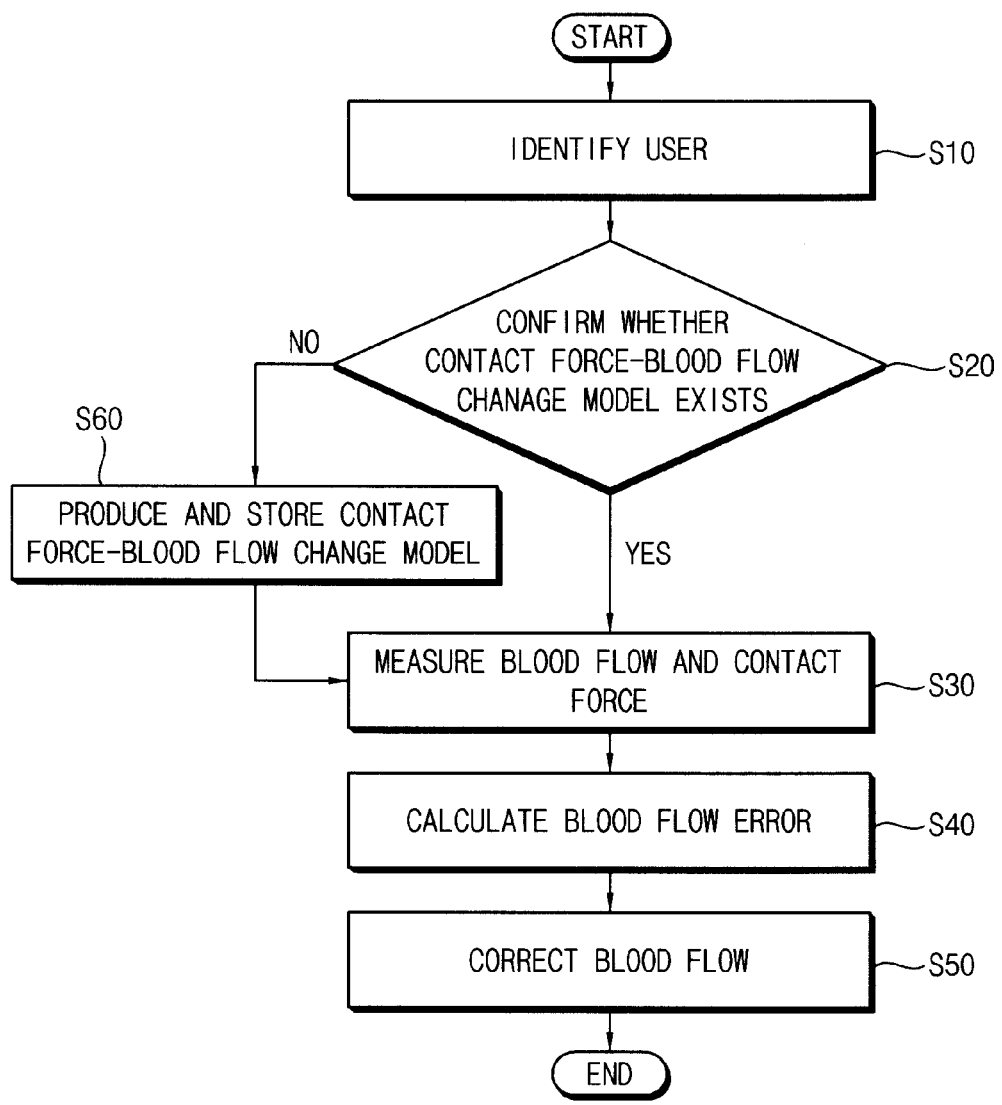

FIG. 4 is a flowchart illustrating a method of measuring blood flow using the blood flow measurement apparatus of FIG. 1 in accordance with example embodiments.

Referring to FIG. 4, in step S10, a user may be identified through the user identification part 50.

When a user inputs his/her fingerprint in the fingerprint recognizer, the user identification part 50 may compare the input fingerprint with the fingerprints stored in the storage part 30, and may identify the user.

In step S20, whether or not a contact force-blood flow change model of the user is stored in the storage part 30 may be confirmed. The blood flow change due to the contact force may be different according to users, and thus a contact force-blood flow change model of each user may be stored in advance to be used in calculation of the blood flow error.

If the contact force-blood flow change model of the user is confirmed, in step S30, a blood flow and a contact force may be measured.

The detection part 10 including the blood flow detector 12 and the force detector 14 may be contacted with a measured portion of the user, and blood flow data and contact force data may be acquired to be transferred to the signal processing part 20. In example embodiments, the blood flow data and the contact force data may include electrical signals and may be stored in the storage part 30.

The blood flow calculator and the contact force calculator of the signal processing part 20 may calculate an average blood flow and an average contact force during a given time or an instant blood flow and an instant contact force from the blood flow data and the contact force data. In an example embodiment, if the contact force is not within a given range, e.g., 1 to 3N, the corresponding blood data may be filtered to be excluded. The calculated blood flow and the calculated contact force may be stored in the storage part 30 and displayed in the display part 40.

In step S40, the error calculator of the signal processing part 20 may calculate an error of the calculated blood flow using the contact force-blood flow change model stored in the storage part 30.

The calculated contact force may be input into the previously stored contact force-blood flow change model so that a blood flow change due to the contact force, i.e., the blood flow error may be calculated. The calculated blood flow error may be stored in the storage part 30 and displayed in the display part 40.

In step S50, the correction calculator of the signal processing part 20 may produce a corrected blood flow in reflection of the calculated blood flow error.

The blood flow calculated by the blood flow calculator may be added or subtracted by the blood flow error calculated by the error calculator, so that the blood flow changed due to the contact force may be corrected to a blood flow at a reference contact force. Thus, a corrected blood flow that has not been changed by the contact force may be measured. The corrected blood flow may be stored in the storage part 30 and displayed in the display part 40.

If the calculated contact force is within a given range, the steps of S30 to S50 may be repeatedly performed. Thus, an average of the corrected blood flow may be calculated so that more exact blood flow may be measured.

If a contact force-blood flow change model of the user is not confirmed in step S20 or the user is not identified in step S10, a contact force-blood flow change model may be newly produced and stored.

A blood flow change may be measured when a contact force is changed, and thus a blood flow change model according to a contact force of a user may be produced. For example, the model may be drafted as a linear function, an exponential function, a fractional function, etc. The produced contact force-blood flow change model may be stored in the storage part 30.

After producing the contact force-blood flow change model, the steps of S30 to S50 may be performed to correct the blood flow.

According to example embodiments, the blood flow measurement apparatus may have a function of correcting a blood flow error due to the contact with the skin, and thus may measure an exact blood flow with no fastening to the skin. Thus, the blood flow measurement apparatus may be easily used for patients with no inconvenience. Additionally, the blood flow measurement apparatus may be applied to a system for predicting whether people or animals are in a good thermal condition or not.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. An apparatus for measuring blood flow, comprising:
   a detection part including,
      a lower plate,
      an adiabatic layer on the lower plate,
         an upper plate on the adiabatic layer, at least a lower portion of the upper plate being surrounded by the adiabatic layer, a blood flow detector for measuring a blood flow of a measured portion of an object, the blood flow detector being on the upper plate and making contact with the measured portion, a thin film adjacent to the upper plate, the thin film having a stress due to an external force, a supporting member directly on the lower plate, the supporting member supporting the thin film, and the supporting member having a first surface in close proximity to the thin film and a second surface opposite to the first surface, the second surface being farther away than the thin film with respect to the measured portion of the object, and a force detector for detecting a contact force between the blood flow detector and the measured portion, the force detector on the thin film, wherein the blood flow detector is only on the upper plate, the upper plate is thicker than the thin film, and the force detector is only on the thin film; and a signal processing part for
calculating a change in the blood flow due to the contact force, and
producing a corrected blood flow in reflection of the calculated change in the blood flow.

2. The apparatus of claim 1, wherein the blood flow detector includes:
a heater for heating the measured portion; and
a thermometer for measuring a temperature of the measured portion.

3. The apparatus of claim 1, wherein the blood flow detector includes:
a light source for emitting a light onto the measured portion; and
a light sensor for detecting a light reflected from the measured portion.

4. The apparatus of claim 1, wherein the force detector includes a piezoelectric element or a capacitive sensor.

5. The apparatus of claim 1, wherein the signal processing part includes:
a contact force-blood flow change model producer for producing a contact force-blood flow change model by modeling the change in the blood flow due to the contact force;
an error calculator for calculating the change in the blood flow due to the contact force using the contact force-blood flow change model;
a correction calculator for producing the corrected blood flow in reflection of the calculated change in the blood flow;
a blood flow calculator for calculating the blood flow from a signal transferred by the blood flow detector; and
a contact force calculator for calculating the contact force from a signal transferred by the force detector.

6. The apparatus of claim 1, further comprising:
a storage part for storing data generated by the detection part and the signal processing part.

7. The apparatus of claim 1, further comprising:
a display part for displaying data generated by the signal processing part.

8. The apparatus of claim 1, further comprising:
a user identification part for identifying a user having the measured portion.

9. A method of measuring blood flow, comprising:
i) measuring a blood flow by applying heat to a measured portion of an object, contacting a blood flow detector with the measured portion, and measuring a temperature change of the measured portion according to a lapse of time, and measuring a contact force between the blood flow detector and the measured portion,
wherein both of the blood flow and the contact force are measured by an apparatus for measuring blood flow, the apparatus including,
a lower plate,
an adiabatic layer on the lower plate,
an upper plate on the adiabatic layer, at least a lower portion of the upper plate being surrounded by the adiabatic layer,
the blood flow detector on the upper plate,
a thin film adjacent to the upper plate, the thin film having a stress due to an external force,
a supporting member directly on the lower plate, the supporting member supporting the thin film, and the supporting member having a first surface in close proximity to the thin film and a second surface opposite to the first surface, the second surface being farther away than the thin film with respect to the measured portion of the object, and
a force detector on the thin film, the force detector measuring the contact force between the blood flow detector and the measured portion of the object,
wherein the blood flow detector is only on the upper plate, the upper plate is thicker than the thin film, and the force detector is only on the thin film;
ii) calculating a change in the blood flow due to the contact force using the measured contact force; and
iii) producing a corrected blood flow in reflection of the calculated change in the blood flow.

10. The method of claim 9, wherein measuring the blood flow and the contact force includes calculating an average blood flow and an average contact force, respectively, during a given time.

11. The method of claim 9, wherein measuring the blood flow and the contact force includes filtering the contact force so that the contact force not within a given range is excluded.

12. The method of claim 9, wherein calculating the change in the blood flow error is performed using a blood flow change model due to a contact force.

13. The method of claim 9, wherein producing the corrected blood flow includes correcting the measured blood flow to a blood flow at a reference contact force by reflecting the calculated change in the blood flow to the blood flow measured at the contact force.

14. The method of claim 9, wherein if the measured contact force is within a given range, the operations of i) to iii) are repeatedly performed.

15. The method of claim 9, further comprising:
identifying a user having the measured portion.

16. The method of claim 15, further comprising:
confirming whether or not a contact force-blood flow change model of the user exists.

17. The method of claim 16, if the contact force-blood flow change model of the user is not confirmed, further comprising:
producing the contact force-blood flow change model by measuring a blood flow of the measured portion while changing a contact force between the blood flow detector and the measured portion; and
storing the contact force-blood flow change model.

18. The method of claim 9, wherein the force detector includes a piezoelectric element.

* * * * *